United States Patent
Chen et al.

(10) Patent No.: US 11,951,286 B2
(45) Date of Patent: Apr. 9, 2024

(54) AUTOMATIC INJECTION DEVICE FOR FLUID

(71) Applicant: BANZA STAMPING INDUSTRY CORP., Suao Township, Yilan County (TW)

(72) Inventors: Li-Wei Chen, Suao Township, Yilan County (TW); Cole Krebs, Suao Township, Yilan County (TW)

(73) Assignee: BANZA STAMPING INDUSTRY CORP., Suao Township (TW)

( * ) Notice: Subject to any disclaimer, the term of this patent is extended or adjusted under 35 U.S.C. 154(b) by 700 days.

(21) Appl. No.: 17/134,239

(22) Filed: Dec. 25, 2020

(65) Prior Publication Data

US 2021/0113767 A1 Apr. 22, 2021

Related U.S. Application Data

(63) Continuation-in-part of application No. 16/005,885, filed on Jun. 12, 2018, now Pat. No. 10,905,830.

(51) Int. Cl.
*A61M 5/20* (2006.01)
*A61M 5/31* (2006.01)
*A61M 5/315* (2006.01)
*A61M 5/32* (2006.01)

(52) U.S. Cl.
CPC ...... *A61M 5/2033* (2013.01); *A61M 5/31513* (2013.01); *A61M 5/3129* (2013.01); *A61M 5/3202* (2013.01)

(58) Field of Classification Search
CPC ............ A61M 5/2033; A61M 5/31513; A61M 5/3129; A61M 5/3202; A61M 5/2053
USPC ........................................................ 604/140
See application file for complete search history.

(56) References Cited

U.S. PATENT DOCUMENTS

| | | | |
|---|---|---|---|
| 2,680,439 A | 6/1954 | Sutermeister | |
| 5,383,851 A * | 1/1995 | McKinnon, Jr. | ........ A61M 5/30 604/143 |
| 2017/0290982 A1 | 10/2017 | Edwards et al. | |

FOREIGN PATENT DOCUMENTS

| | | |
|---|---|---|
| CN | 87105155 A | 1/1988 |
| TW | 200303224 A | 9/2003 |

* cited by examiner

*Primary Examiner* — Michael J Tsai
*Assistant Examiner* — Nidah Hussain
(74) *Attorney, Agent, or Firm* — patenttm.us

(57) ABSTRACT

An automatic injection device for fluid has a sleeve, an actuating unit, a barrel with a piercing needle and a high-pressure air source. The high-pressure air source is mounted slidably in the barrel. The actuating unit is mounted in the sleeve and barrel and selectively blocks the high-pressure air source. When the user needs to release the high-pressure air in the high-pressure air source, the user press the actuating unit to allow the high-pressure air source to slide until the high-pressure air source hits the piercing needle. Therefore, the high-pressure air in the high-pressure air source is easily released by actuate the actuating unit without additional hand tools.

19 Claims, 16 Drawing Sheets

AUTOMATIC INJECTION DEVICE FOR FLUID

CROSS-REFERENCE TO RELATED APPLICATIONS

This application is a continuation in part application of United States patent application filed on Jun. 12, 2018 and having application Ser. No. 16/005,885, the entire contents of which are hereby incorporated herein by reference.

BACKGROUND OF THE INVENTION

1. Field of the Invention

The present invention is an automatic injection device, specifically an automatic injection device for fluid.

2. Description of the Prior Arts

Pneumatic devices usually comprise a high-pressure air source therein to be actuated to instantly release the high pressure air to pushes the liquid out. The high-pressure air source is sealed before being assembled in the pneumatic device. After the high-pressure air source is assembled in the pneumatic device, the user needs to use a hand tool to unseal the high-pressure air source so that the compressed air in the high-pressure air source could come out to pushes the liquid out. However, using the hand tool to unseal the high-pressure air source is inconvenient for the user, especially for pneumatic medical device.

To overcome the shortcomings, the present invention provides an automatic injection device for fluid to mitigate or to obviate the aforementioned problems.

SUMMARY OF THE INVENTION

The objective of the present invention is to provide an automatic injection device for fluid to allow easily use. The automatic injection device for fluid has a sleeve, an actuating unit, a barrel with a piercing needle and a high-pressure air source. The high-pressure air source is mounted slidably in the barrel. The actuating unit is mounted in the sleeve and barrel and selectively blocks the high-pressure air source. When the user needs to release the high-pressure air in the high-pressure air source, the user press the actuating unit to allow the high-pressure air source to slide until the high-pressure air source hits the piercing needle. Therefore, the high-pressure air in the high-pressure air source is easily released by actuate the actuating unit without additional hand tools.

Other objectives, advantages and novel features of the invention will become more apparent from the following detailed description when taken in conjunction with the accompanying drawings.

DETAILED DESCRIPTION OF THE EMBODIMENTS

Figure 1:
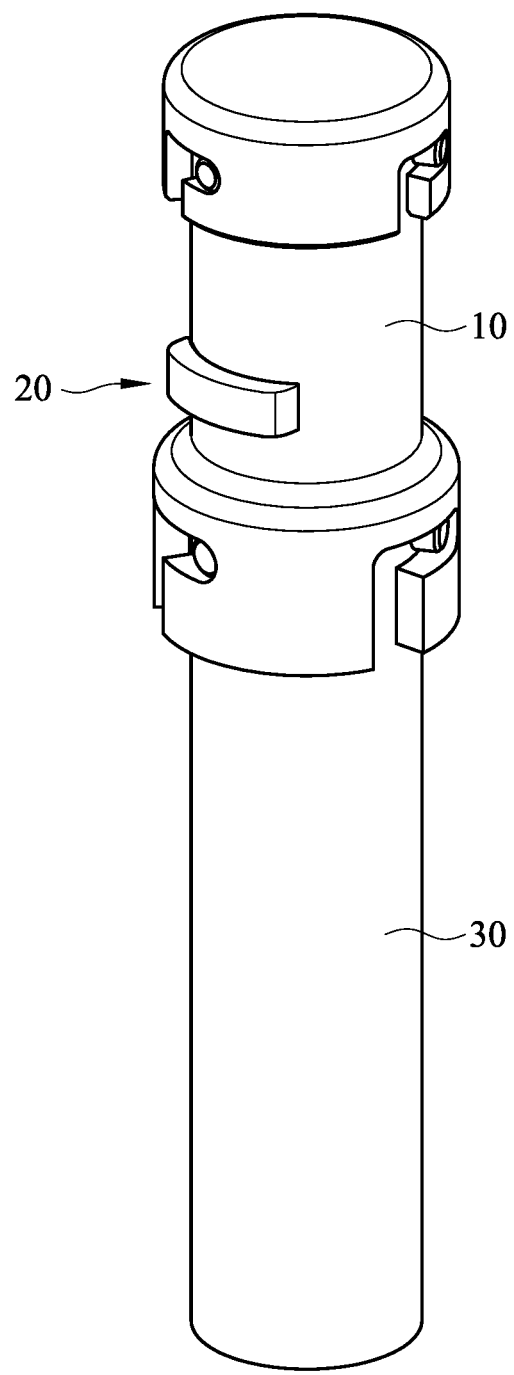
FIG. 1 is a perspective view of an automatic injection device for fluid in accordance with the present invention.
Figure 2:
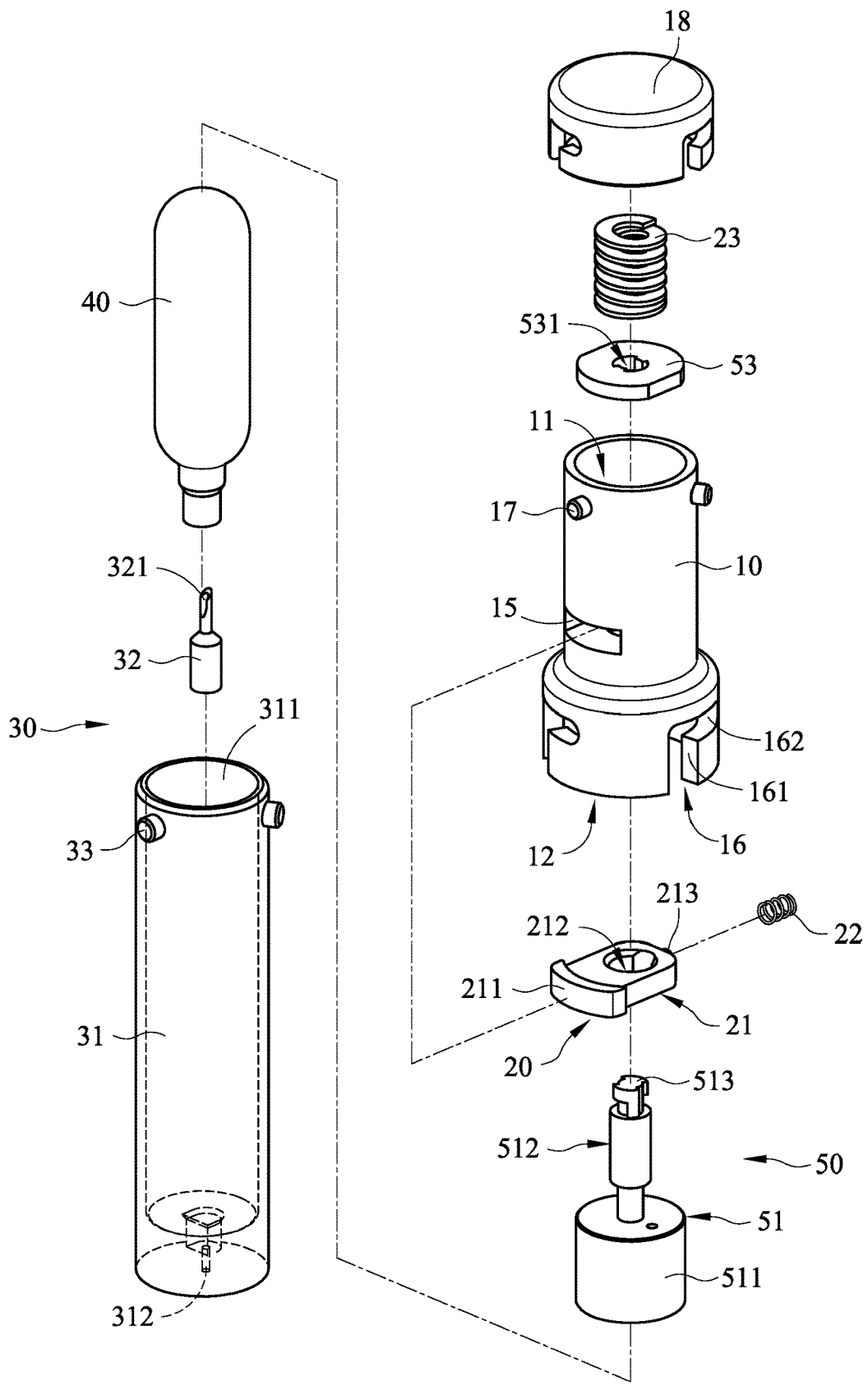
FIG. 2 is an exploded perspective view of the automatic injection device for fluid in FIG. 1.

With reference to FIGS. 1 and 2, a first embodiment of an automatic injection device for fluid in accordance with the present invention comprises a sleeve 10, an actuating unit 20, a barrel 30, a high-pressure air source 40 and a driven unit 50.

The sleeve 10 is hollow and has an inside wall, an outside wall, a first end opening 11, a second end opening 12, a side hole 15, multiple lock holes 16, multiple lock protrusions 17 and a cap 18. The side hole 15 is formed transversely through the sleeve 10. The lock holes 16 are formed transversely through the sleeve 10. Each lock hole 16 has a longitudinal part 161 and a lateral part 162 communicating with the longitudinal part 161. The longitudinal part 161 of each lock hole 16 communicates with the second end opening 12 of the sleeve 10. The lock protrusions 17 are transversely formed separately on the outside wall of the sleeve 10. The cap 18 is mounted on the first end opening 11 of the sleeve 10 and may be held by the lock protrusions 17.

Figure 3:
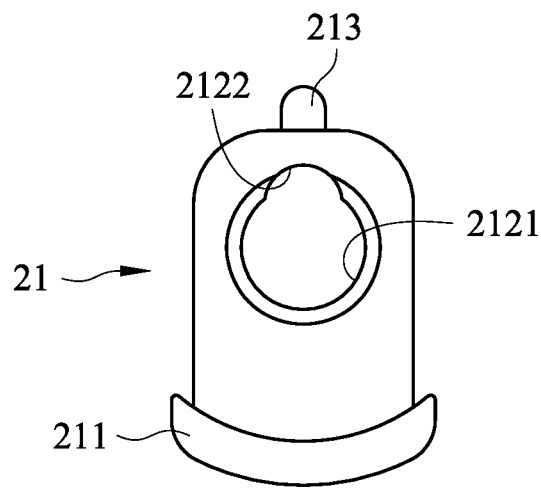
FIG. 3 is a top view of an actuating washer of the automatic injection device for fluid in FIG. 1.

With reference to FIGS. 1 to 3, the actuating unit 20 is mounted in the sleeve 10. The actuating unit 20 has an actuating washer 21, a resisting resilient element 22 and an actuating resilient element 23. The actuating washer 21 is mounted slidably through the side hole 15 of the sleeve 10 and has a distal end, a proximal end, an enlarged head 211, a limiting unit and a mounting tag 213. The enlarged head 211 is formed on the distal end of the actuating washer 21 and protrudes out of the side hole 15. The limiting unit is defined in the sleeve 10 and may be a through hole 212 formed through the actuating washer 21, located in the sleeve 10 and having a larger part 2121 and a smaller part 2122. The larger part 2121 of the through hole 212 is near the distal end while the smaller part 2122 is near the proximal end. The larger part 2121 and the smaller part 2122 communicate with each other and an inner diameter of the larger part 2121 is larger than an inner diameter of the smaller part 2122. The mounting tag 213 is formed on the proximal end. The resisting resilient element 22 is mounted around the mounting tag 213 and is pressed between the proximal end of the actuating washer 21 and the inside wall of the sleeve 10. The actuating resilient element 23 is mounted in the sleeve 10 and is pressed against the cap 18.

With reference to FIGS. 1 and 2, the barrel 30 is selectively held on the second end opening 12 of the sleeve 10 and may comprise a body 31, a piercing needle 32 and multiple protruding parts 33. The body 31 is hollow and has an inside wall, an outside wall, a first end opening 311, a second end and a slot 312. The slot 312 is formed through the second end of the body 31. The piercing needle 32 is attached to the second end of the body 31 and may have a central hole 321 communicating with the slot 312 of the body 31. The protruding parts 33 are transversely formed separately on the outside wall of the body 31 and selectively slide into the lock holes 16 of the sleeve 10.

The high pressure air source 40 is mounted slidably in the body 31 of the barrel 30.

Figure 4:
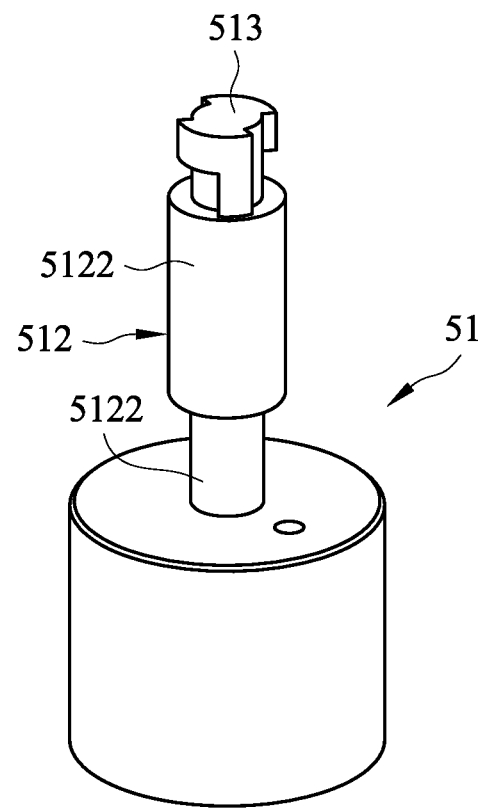
FIG. 4 is a perspective view of a piston of the automatic injection device for fluid in FIG. 1.
Figure 5:
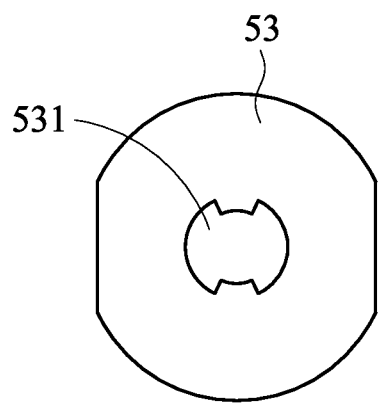
FIG. 5 is a top view of a washer of the automatic injection device for fluid in FIG. 16.

With reference to FIGS. 2, 4 and 5, the driven unit 50 is mounted slidably in the barrel 30 is attached to the high-pressure air source 40, is selectively held by the limiting unit and is selectively actuated by the actuating unit 20 to slide toward the second end of the barrel 30. In one embodiment, the driven unit 50 may comprise a piston 51 and a washer 53. The piston 51 is attached to the high-pressure air source 40 and has a crown 511, a shaft 512 and a cam 513. The crown 511 is attached to the high-pressure air source 40. The shaft 512 is formed longitudinally on the crown 511 and has a thinner segment 5121 and a thicker segment 5122. The thinner segment 5121 is formed longitudinally on the crown 211 and selectively aligns with the smaller part 2122 of the through hole 212 of the actuating washer 21. The thicker segment 5122 is formed longitudinally on, aligns with the thinner segment 5121 and selectively aligns with the larger part 2121 of the through hole 212 of the actuating washer 21. The cam 513 is formed on an end of the thicker segment 5122. The washer 53 is secured on the piston 51 via a cam hole 531 penetrated by the cam.

Figure 6:
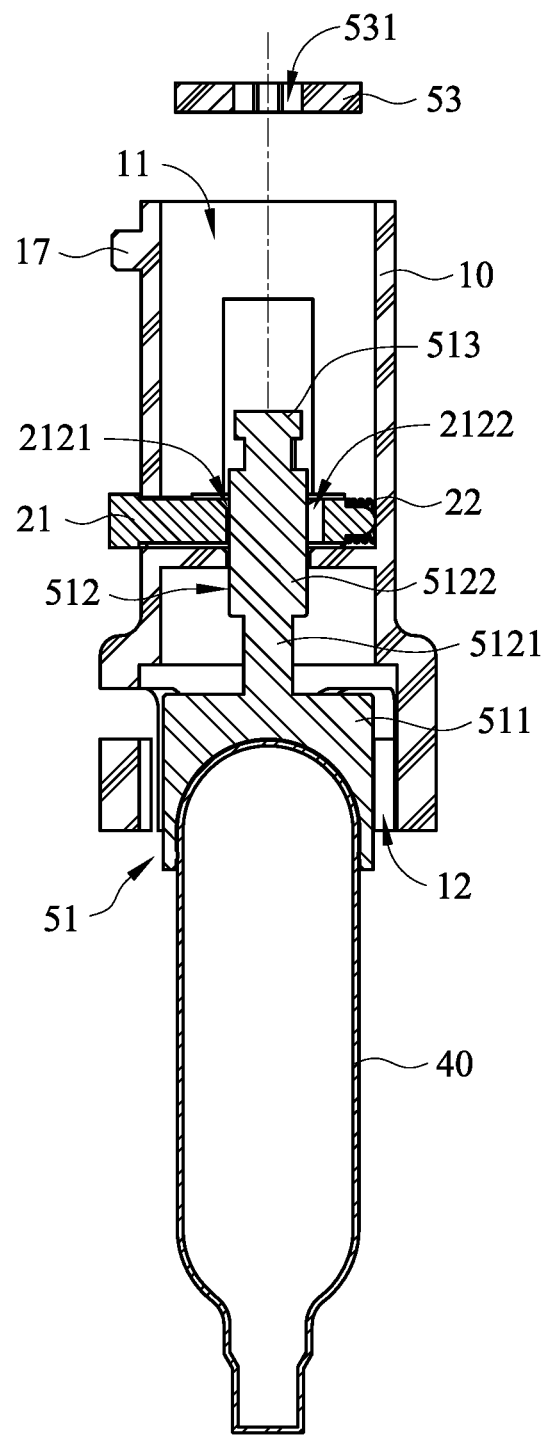
FIG. 6 is an operational side view in partial section of the automatic injection device for fluid in FIG. 1, showing that the piston and a high-pressure air source is mounted into a sleeve.
Figure 7:
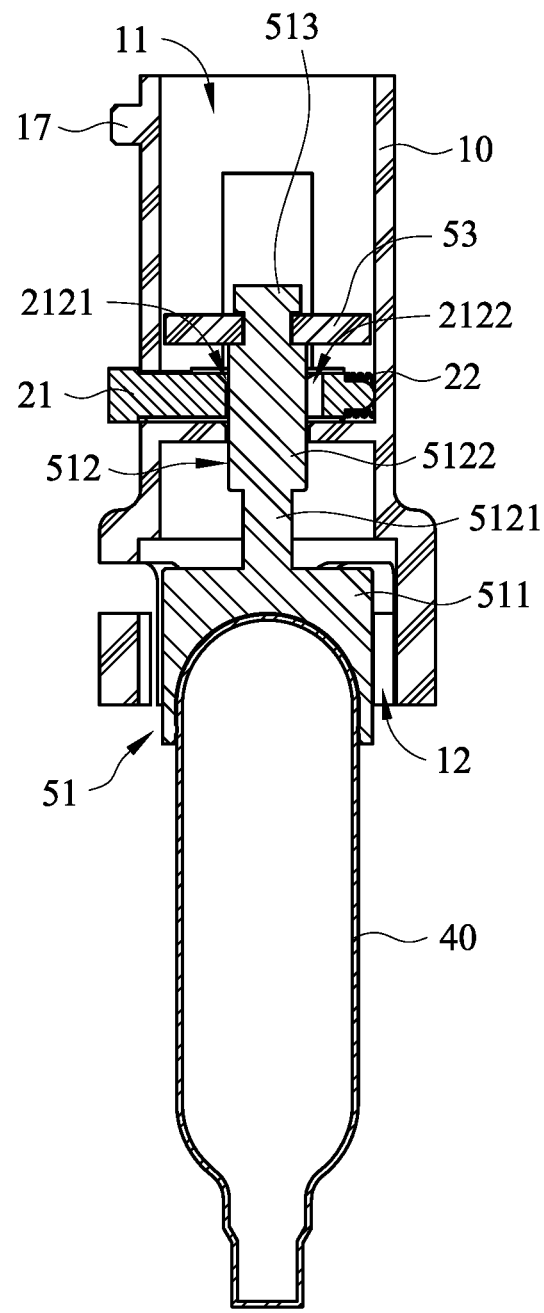
FIG. 7 is an operational side view in partial section of the automatic injection device for fluid in FIG. 1, showing that the washer is mounted into the sleeve.

With reference to FIGS. 6 and 7, the high-pressure air source 40 is attached to the crown 511 of the piston 51. The piston 51 with the high-pressure air source 40 is mounted into the sleeve 10 through the second end opening 12. The thicker segment 5122 of the shaft 512 of the piston 51 is mounted in the larger part 2121 of the through hole 212 of the actuating washer 21 to keep the actuating washer 21 from pushing outward by the resisting resilient element 22. The washer 53 is mounted into the sleeve 10 through the first end opening 11 and aligns the cam hole 531 with the cam 513 to mounted around the piston 51. Then the piston 51 is rotated to misalign the cam 513 and the cam hole 531 so that the washer 53 is secured around the piston 51.

Figure 8:
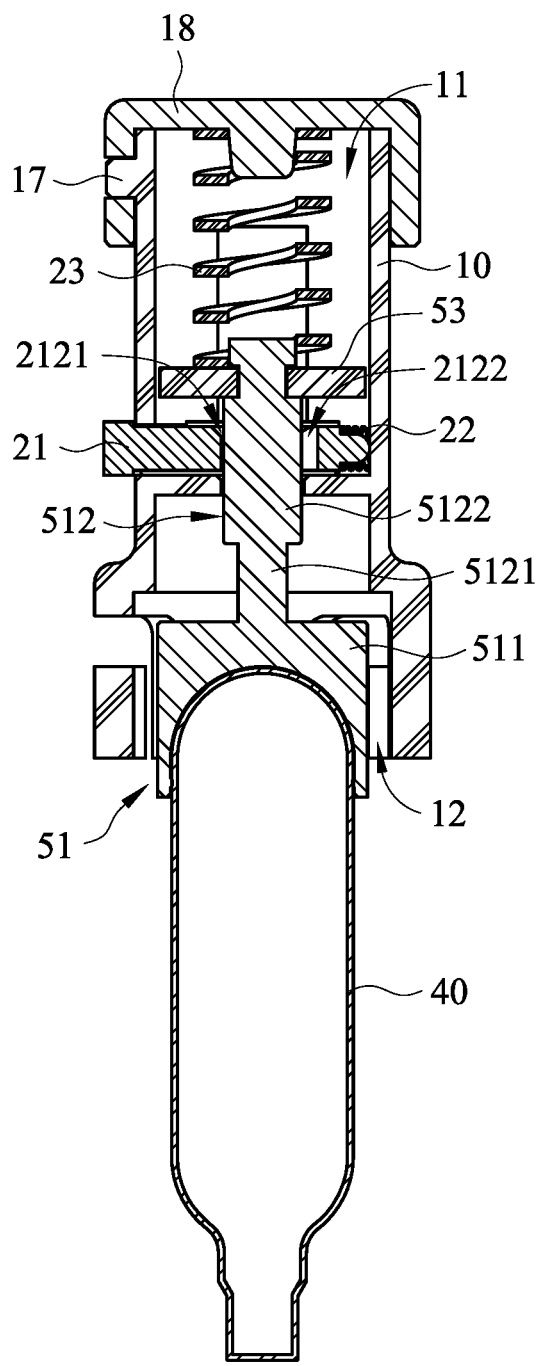
FIG. 8 is an operational side view in partial section of the automatic injection device for fluid in FIG. 1, showing that an actuating resilient element is mounted in the sleeve.

With reference to FIG. 8, the actuating resilient element 23 and the cap 18 are mounted into the first end opening 11. The actuating resilient element 23 is clamped between the washer 53 and the cap 18.

Figure 9:
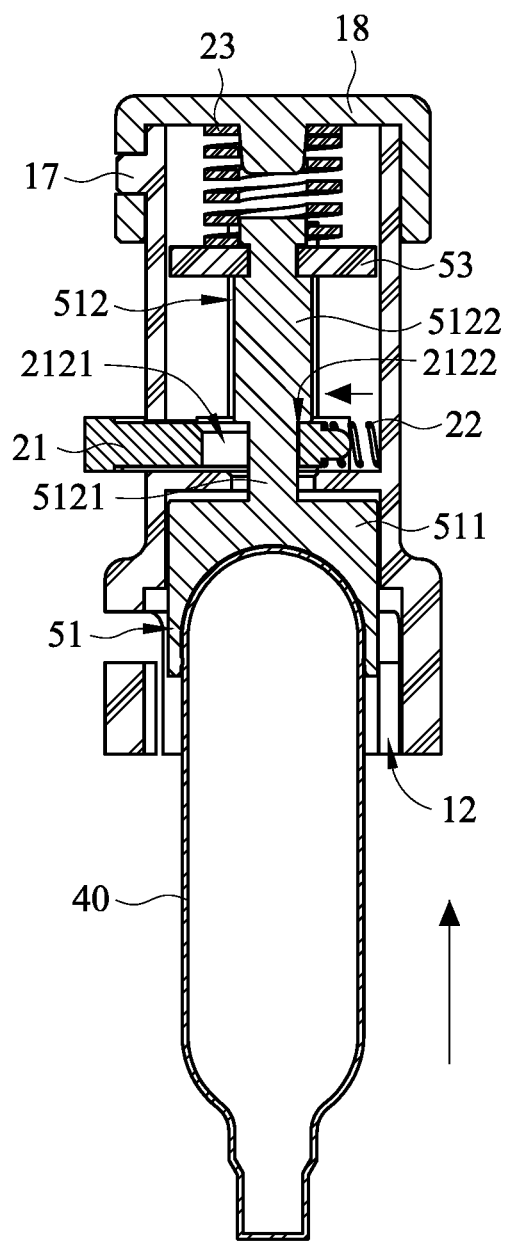
FIG. 9 is an operational side view in partial section of the automatic injection device for fluid in FIG. 1, showing that the piston and the high-pressure air source are pushed upward to be locked in position.

With reference to FIG. 9, the high-pressure air source 40 is pushed upward to force the piston 51 to move upward. Then the shaft 512 is moved upward and the thicker segment 5121 passes through the through hole 212 of the actuating washer 21. When the thicker segment 5122 leaves the through hole 212 and the thinner segment 5121 reaches the through hole 212, the resisting resilient element 22 releases its resilient force to push the actuating washer 21 to move outward. Then the smaller part 2122 of the through hole 212 aligns with the thinner segment 5121 of the shaft 512 to keep the thicker segment 5122 of the shaft 512 from moving into the through hole 212 so that the thicker segment 5122 abuts against the upper surface of the actuating washer 21. In the mean time, the actuating resilient element 22 is compressed by the washer 53 to restore the resilient force. Since the thicker segment 5122 of the shaft 512 abuts against the upper surface of the actuating washer 21, the shaft 512 is kept from moving downward even though the actuating resilient element 22 presses against the washer 53.

Figure 10:
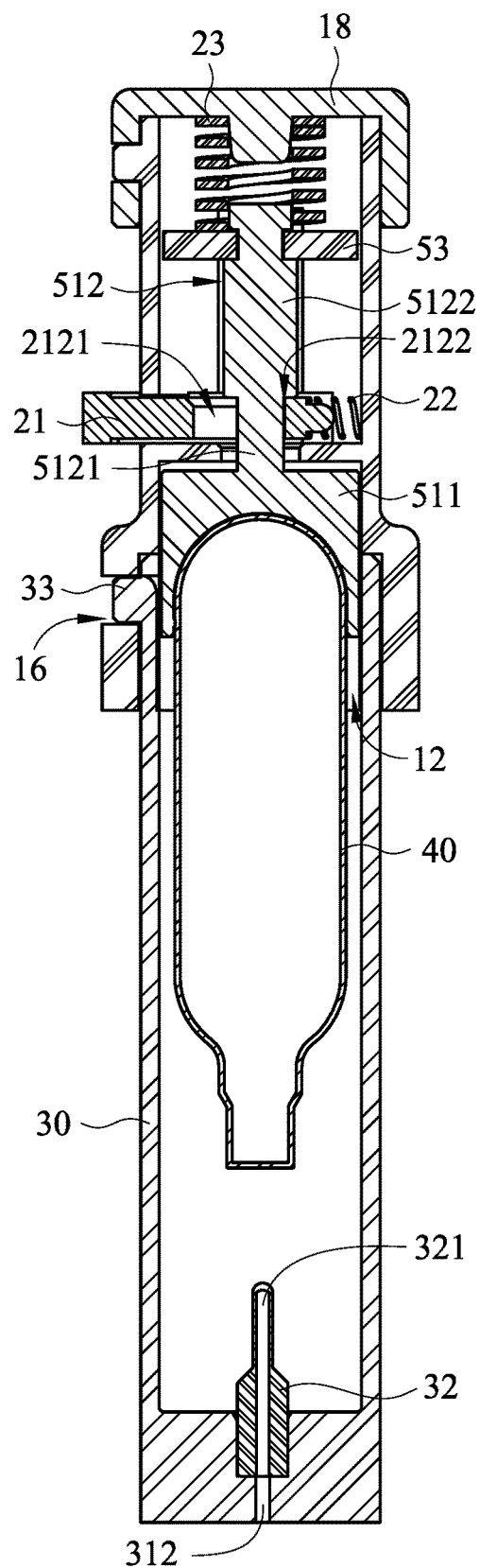
FIG. 10 is an operational side view in partial section of the automatic injection device for fluid in FIG. 1, showing that a barrel is mounted around the high-pressure air source.

With reference to FIG. 10, the barrel 30 is mounted into the second end opening 12 of the sleeve 10 to be mounted around the high-pressure source 40. The barrel 30 is rotated to engage the protruding parts 33 in the lock holes 16 so that the barrel 30 is secured around the high-pressure air source 40.

Figure 11:
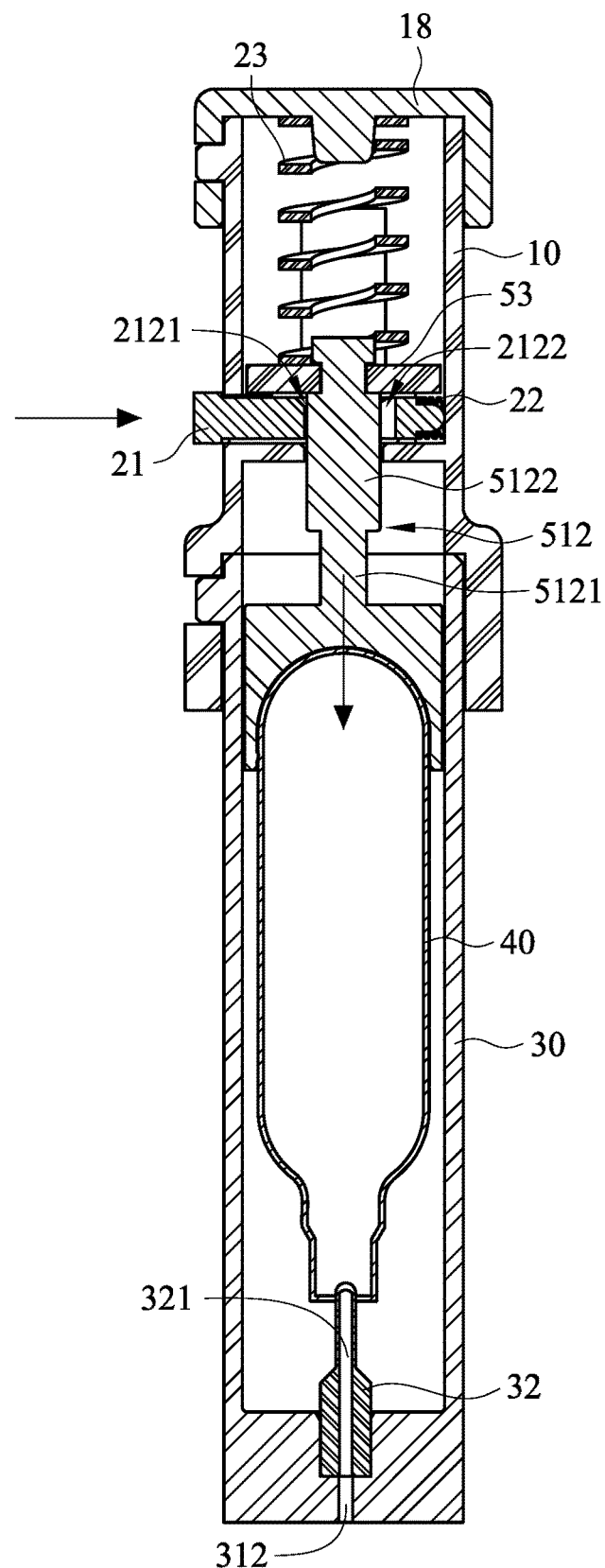
FIG. 11 is an operational side view in partial section of the automatic injection device for fluid in FIG. 1, showing that an actuating unit is actuated to push the piston and the high-pressure air source to move downward.

With reference to FIG. 11, the user press the actuating washer 21 when the user needs to release the high-pressure air in the high-pressure air source 40. The actuating washer 21 is pressed into the sleeve 10 to align the larger part 2121 of the through hole 212 with the thicker segment 5122 of the shaft 512 so that the thicker segment 5122 is allowed to pass through the through hole 212 again. Then the actuating resilient element 23 releases its resilient force to push the shaft 512 to move downward with the thicker segment 5122 of the shaft 512 passing through the larger part 2121 of the through hole 212. Thus, the piston 51 along with the high-pressure air source 40 are pushed toward the second end opening 12 of the sleeve 10 and toward the second end of the body 31 of the barrel 30 until an end of the high-pressure air source 40 hits the piercing needle 32. Then the end of the high-pressure air source 40 is punctured through by the piercing needle 32 to release the high-pressure air in the high-pressure air source 40 through the central hole 321 of the piercing needle 32 and the slot 312 of the body 31 of the barrel 30 so that the fluid in the associate device is injected to the subject via the pneumatic force of the high-pressure air.

Figure 12:
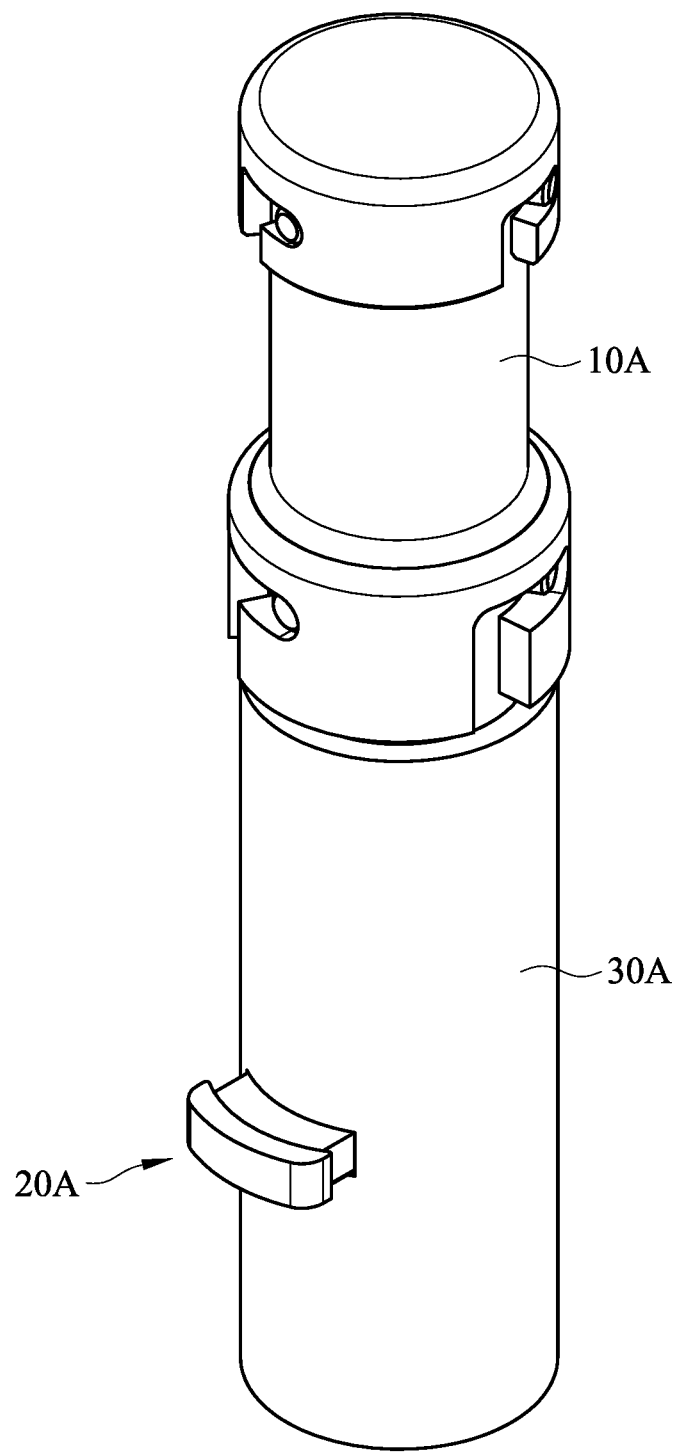
FIG. 12 is a perspective view of another embodiment of an automatic injection device for fluid in accordance with the present invention.
Figure 13:
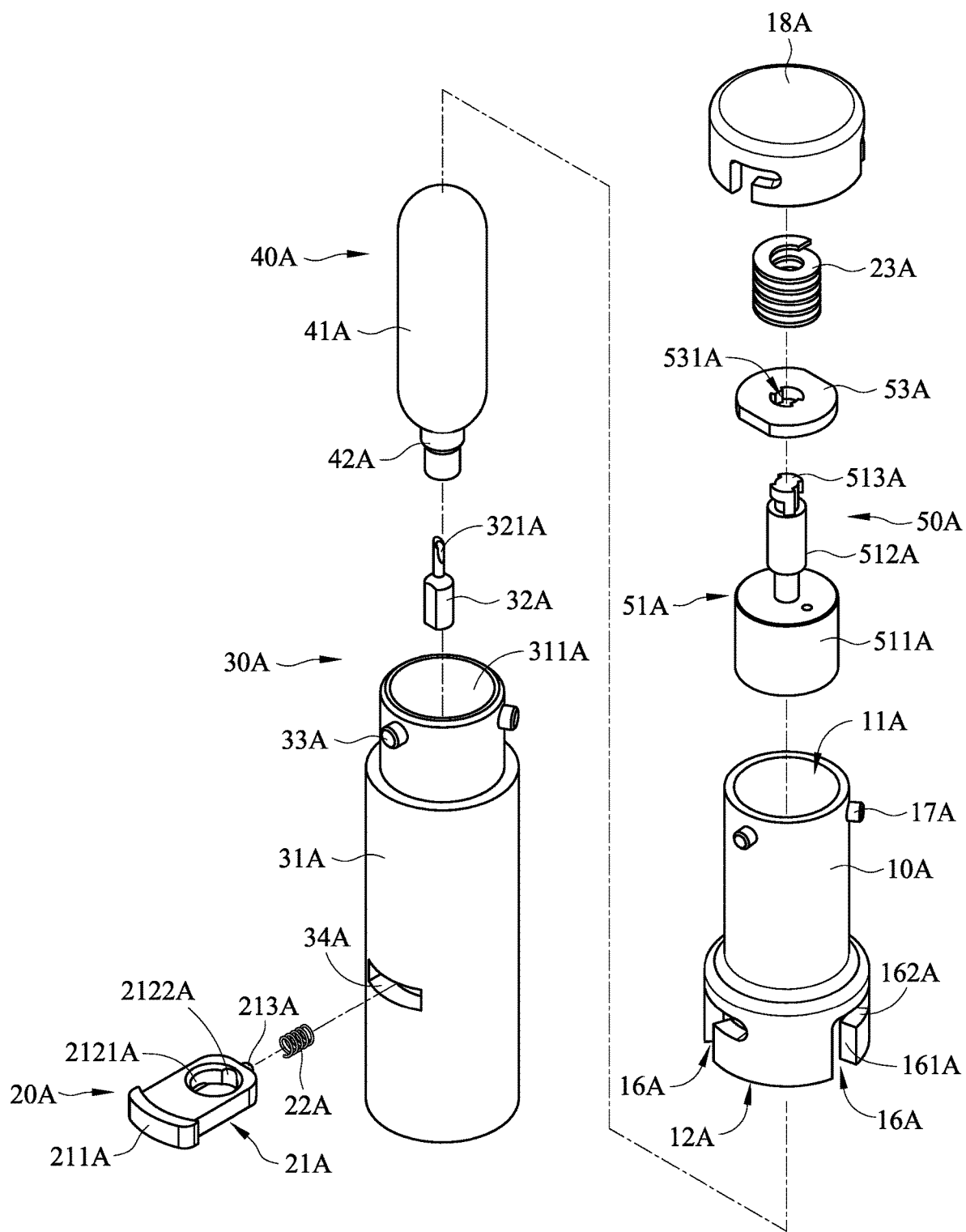
FIG. 13 is an exploded perspective view of the automatic injection device for fluid in FIG. 12.

With reference to FIGS. 12 and 13, a second embodiment of an automatic injection device for fluid in accordance with the present invention comprises a sleeve 10A, an actuating unit 20A, a barrel 30A, a high-pressure air source 40A and a driven unit 50A.

The sleeve 10A is hollow and has an inside wall, an outside wall, a first end opening 11A, a second end opening 12A, multiple lock holes 16A, multiple lock protrusions 17A and a cap 18A. The lock holes 16A are formed transversely through the sleeve 10A. Each lock hole 16A has a longitudinal part 161A and a lateral part 162A communicating with the longitudinal part 161A. The longitudinal part 161A of each lock hole 16A communicates with the second end opening 12A of the sleeve 10A. The lock protrusions 17A are transversely formed separately on the outside wall of the sleeve 10A. The cap 18A is mounted on the first end opening 11A of the sleeve 10A and may be held by the lock protrusions 17A.

Figure 14:
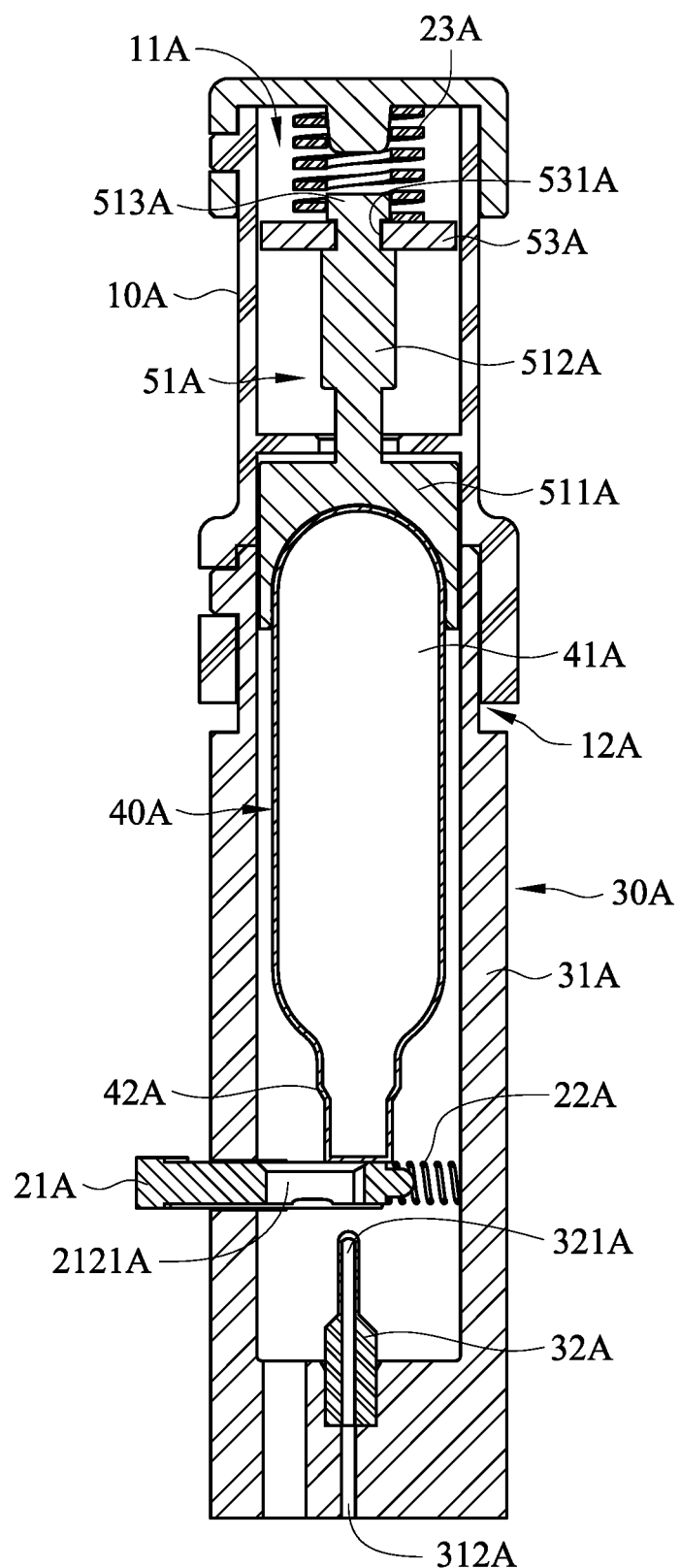
FIG. 14 is a side view in partial section of the automatic injection device for fluid in FIG. 12.

With reference to FIGS. 12 to 14, the barrel 30A is selectively held on the second end opening 12A of the sleeve 10A and has a side hole 34A. The side hole 34A is formed transversely through the barrel 30A. The barrel 30A may comprise a body 31A, a piercing needle 32A and multiple protruding parts 33A. The body 31A is hollow and has an inside wall, an outside wall, a first end opening 311A, a second end and a slot 312A. The side hole 34A is formed transversely through the body 31A. The slot 312A is formed through the second end of the body 31A. The piercing needle 32A is attached to the second end of the body 31A and may have a central hole 321A communicating with the slot 312A of the body 31A. The protruding parts 33A are transversely formed separately on the outside wall of the body 31A and selectively slide into the lock holes 16A of the sleeve 10A.

With reference to FIGS. 12 and 13, the actuating unit 20A is mounted in the sleeve 10A and the barrel 30A. The actuating unit 20A has an actuating washer 21A, a resisting resilient element 22A and an actuating resilient element 23A. The actuating washer 21A is mounted slidably through the side hole 34A of the barrel 30A and has a distal end, a proximal end, an enlarged head 211A, a limiting unit and a mounting tag 213A. The enlarged head 211A is formed on the distal end of the actuating washer 21A and protrudes out of the side hole 34A. The limiting unit is defined in the barrel 30A and may be a through hole 212A formed through the actuating washer 21A, located in the barrel 30A and having a larger part 2121A and a smaller part 2122A. The larger part 2121A of the through hole 212A is near the distal end while the smaller part 2122A is near the proximal end. The larger part 2121A and the smaller part 2122A communicate with each other and an inner diameter of the larger part 2121A is larger than an inner diameter of the smaller part 2122A. The mounting tag 213A is formed on the proximal end. The resisting resilient element 22A is mounted around the mounting tag 213A and is pressed between the proximal end of the actuating washer 21A and an inside wall of the body 31A of the barrel 30A. The actuating resilient element 23A is mounted in the sleeve 10A and is pressed against the cap 18A.

The high pressure air source 40A is mounted slidably in the body 31A of the barrel 30A and selectively abuts against the actuating washer 21A. The high pressure air source 40A has a body 41A and a neck 42A. An outer diameter of the neck 42A is smaller than an outer diameter of the body 41A. The outer diameter of the neck 42A is larger than the inner diameter of the smaller part 2122A and is smaller than the inner diameter of the larger part 2121A of the through hole 212A of the actuating washer 21A.

With reference to FIG. 13, the driven unit 50A is mounted slidably in the barrel 30A, is attached to the high-pressure air source 40A and is selectively actuated by the actuating unit 20A to slide toward the second end of the barrel 30A. In one embodiment, the driven unit 50 may comprise a piston 51A and a washer 53A. The piston 51A is attached to the high-pressure air source 40A and has a crown 511A, a shaft 512A and a cam 513A. The crown 511A is attached to the high-pressure air source 40A. The shaft 512A is formed longitudinally on the crown 511A. The cam 513A is formed on an end of the shaft 512A. The washer 53A is secured on the piston 51A via a cam hole 531A penetrated by the cam 513A.

With reference to FIGS. 13 and 14, the high-pressure air source 40A is attached to the crown 511A of the piston 51A. The piston 51A with the high-pressure air source 40A is mounted into the sleeve 10A through the second end opening 12A. The washer 53A is mounted into the sleeve 10A through the first end opening 11A and aligns the cam hole 531A with the cam 513A to be mounted around the piston 51A. Then the piston 51A is rotated to misalign the cam 513A and the cam hole 531A so that the washer 53A is secured around the piston 51A. The actuating resilient element 23A and the cap 18A are mounted into the first end opening 11A. The actuating resilient element 23A is clamped between the washer 53A and the cap 18A. The high-pressure air source 40A is pushed upward to force the piston 51A to move upward. The resisting resilient element 22A releases its resilient force to push the actuating washer 21A to move outward through the side hole 34A, and the high pressure air source 40A aligns with the smaller part 2122A of the through hole 212A of the actuating washer 21A. The high pressure air source 40A abuts against the actuating washer 21A since the outer diameter of the neck 42A of the high pressure air source 40A is larger than the inner diameter of the smaller part 2122A of the through hole 212A of the actuating washer 21A. Thus, the shaft 512A is kept from moving downward via the block of the actuating washer 21A even though the actuating resilient element 22A presses against the washer 53A.

Figure 15:
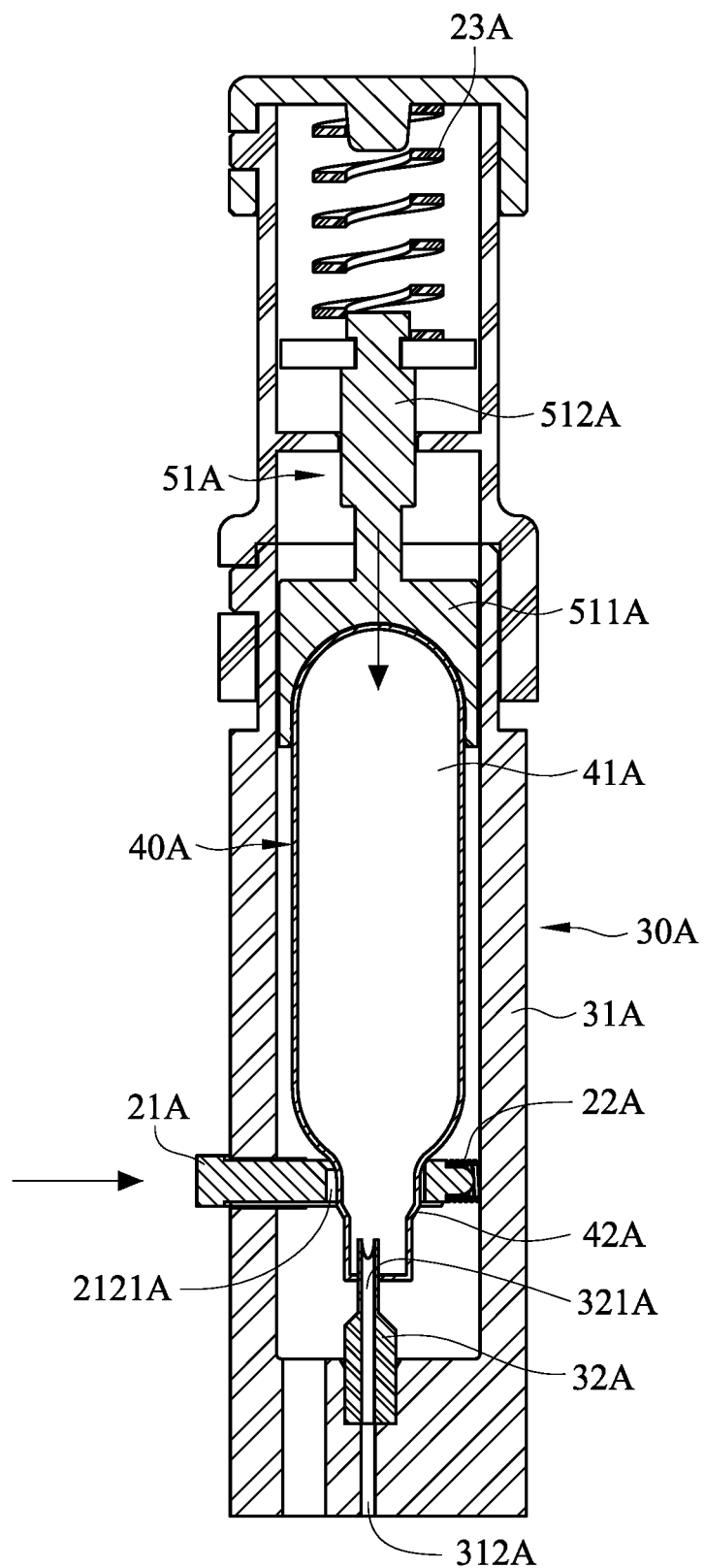
FIG. 15 is an operational side view in partial section of the automatic injection device for fluid in FIG. 12, showing that an actuating unit is actuated to push the piston and the high-pressure air source to move downward.

With reference to FIGS. 13 and 15, the user press the actuating washer 21A when the user needs to release the high-pressure air in the high-pressure air source 40A. The actuating washer 21A is pressed into the barrel 30A to align the larger part 2121A of the through hole 212A with the neck 42A of the high pressure air source 40A so that the neck 42A of the high pressure air source 40A is allowed to pass through the through hole 212A. Then the actuating resilient element 23A releases its resilient force to push the shaft 512A to move downward with the neck 42A of the high pressure air source 40A passing through the larger part 2121A of the through hole 212A. Thus, the piston 51A along with the high-pressure air source 40A are pushed toward the second end opening 12A of the sleeve 10A and toward the second end of the body 31A of the barrel 30A until an end of the high-pressure air source 40A hits the piercing needle 32A. Then the end of the high-pressure air source 40A is punctured through by the piercing needle 32A to release the high-pressure air in the high-pressure air source 40A through the central hole 321A of the piercing needle 32A and the slot 312A of the body 31A of the barrel 30A so that the fluid in the associate device is injected to the subject via the pneumatic force of the high-pressure air.

Figure 16:
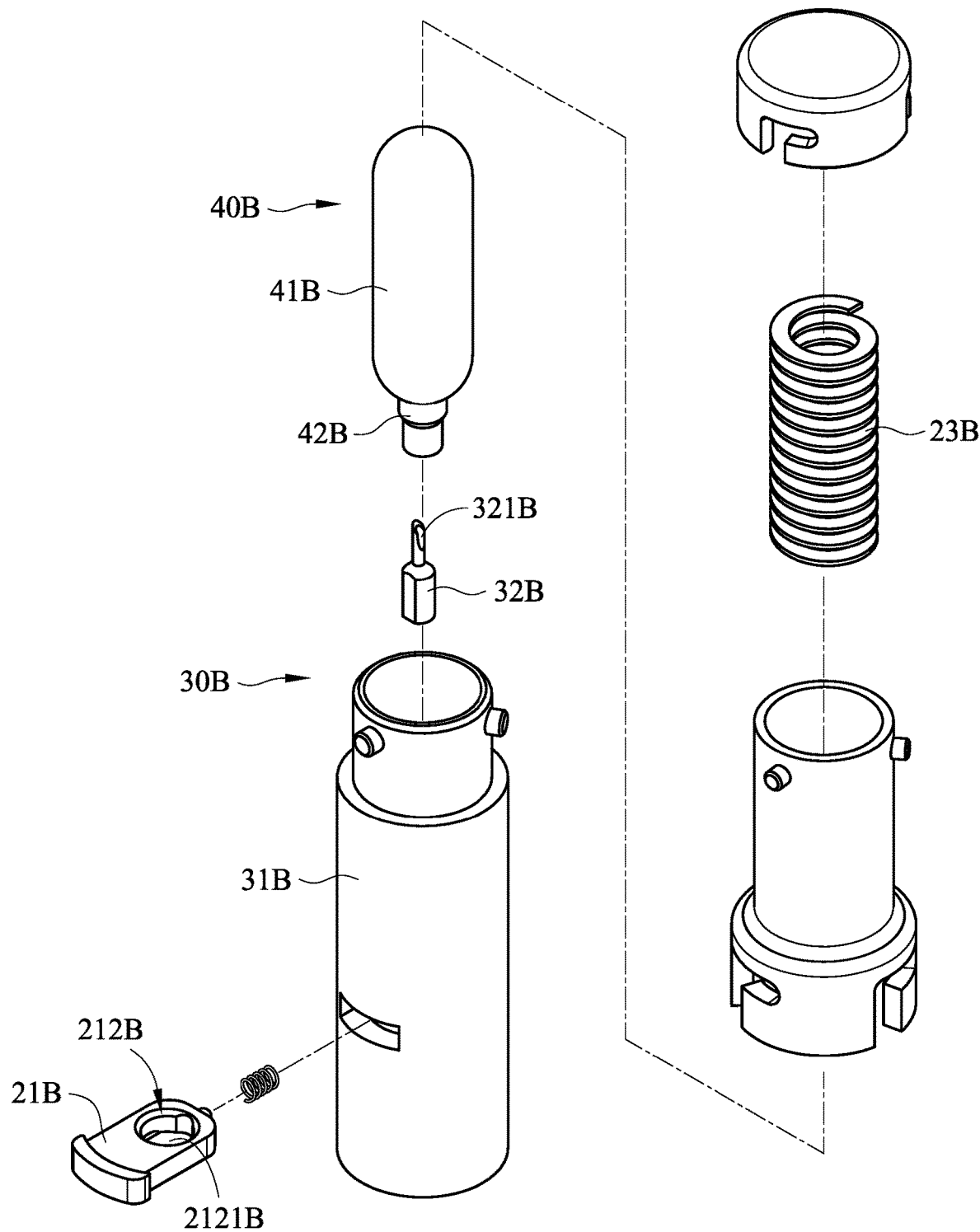
FIG. 16 is an exploded perspective view of still another embodiment of an automatic injection device for fluid in accordance with the present invention.
Figure 17:
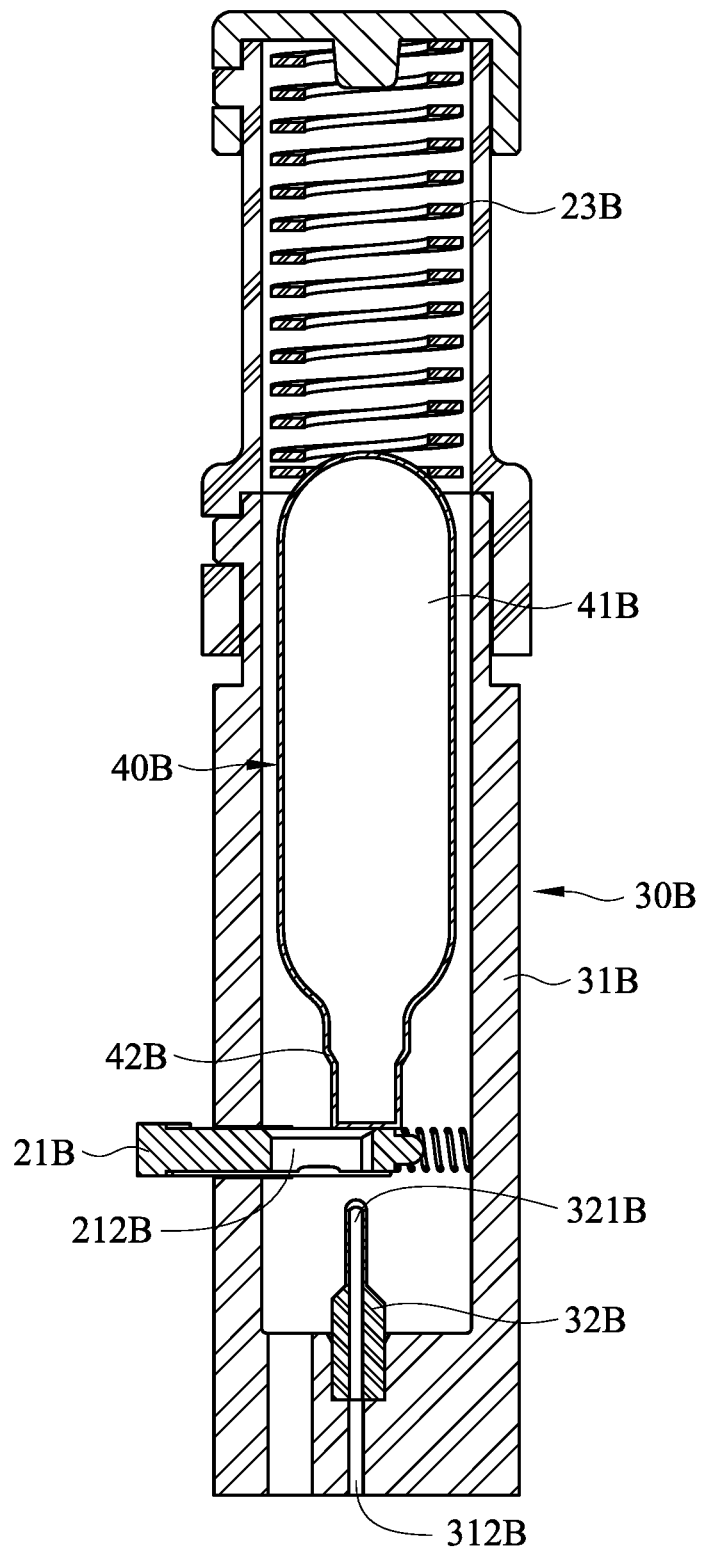
FIG. 17 is a side view in partial section of the automatic injection device for fluid in FIG. 16.
Figure 18:
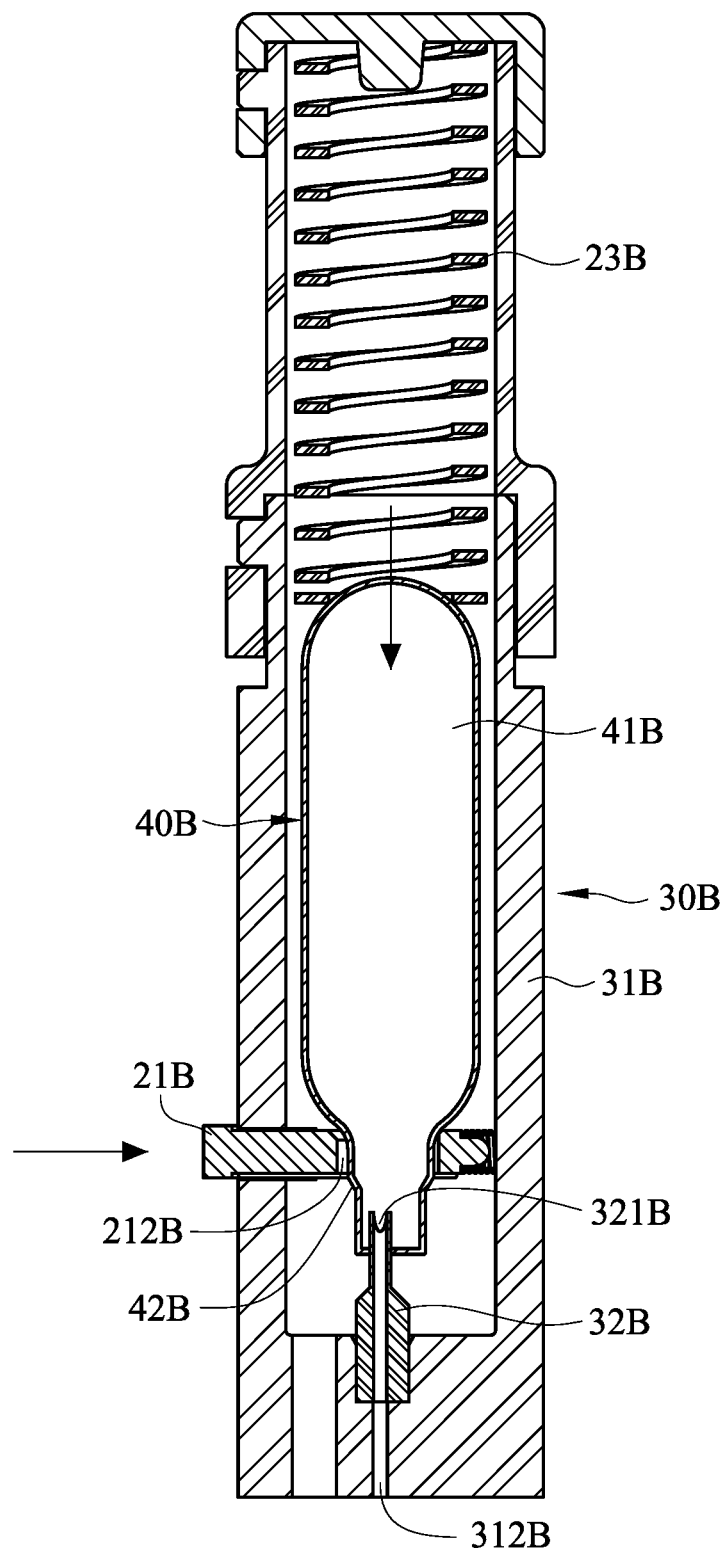
FIG. 18 is an operational side view in partial section of the automatic injection device for fluid in FIG. 16, showing that an actuating unit is actuated to push the piston and the high-pressure air source to move downward.

With reference to FIGS. 16 and 17, a third embodiment of an automatic injection device for fluid in accordance with the present invention has similar structure with the second embodiment as shown in FIGS. 12 to 15 without the driven unit 50A. The actuating resilient element 23B directly abuts against the high pressure air source 40B. The user press the actuating washer 21B when the user needs to release the high-pressure air in the high-pressure air source 40B. The actuating washer 21B is pressed into the barrel 30B so that the neck 42B of the high pressure air source 40B is allowed to pass through the through hole 212B. Then the actuating resilient element 23B releases its resilient force to push the body 41B the high pressure air source 40B passing through the larger part 2121B of the through hole 212B. Thus, the high-pressure air source 40B are pushed toward the second end of the body 31B of the barrel 30B until an end of the high-pressure air source 40B hits the piercing needle 32B.

Then the high-pressure air in the high-pressure air source 40B is released through the central hole 321B of the piercing needle 32B and the slot 312B of the body 31B of the barrel 30B so that the fluid in the associate device is injected to the subject via the pneumatic force of the high-pressure air.

The advantages of the automatic injection device for fluid as described are recited as follow. With the cooperation of the actuating unit 20, 20A, 20B, the high-pressure air in the high-pressure air source 40, 40A, 40B is easily released by actuate the actuating unit 20, 20A, 20B without additional hand tools. Therefore, the user can use the automatic injection device for fluid as described to inject the fluid in the associate device conveniently.

Even though numerous characteristics and advantages of the present invention have been set forth in the foregoing description, together with details of the structure and features of the invention, the disclosure is illustrative only. Changes may be made in the details, especially in matters of shape, size, and arrangement of parts within the principles of the invention to the full extent indicated by the broad general meaning of the terms in which the appended claims are expressed.

What is claimed is:

1. An automatic injection device for fluid comprising:
    a hollow sleeve and having
        a first end opening;
        a second end opening; and
        a cap mounted on the first end opening;
    a barrel selectively held on the second end opening of the sleeve and having
        a body having a first end opening and a second end;
        a side hole formed transversely through the body of the barrel;
        a piercing needle attached to the second end of the body;
    an actuating unit mounted slidably in the barrel and having
        an actuating washer mounted slidably through the side hole of the barrel and having
            a distal end;
            a proximal end; and
            a through hole formed through the actuating washer, located in the sleeve and having a larger part near the distal end of the actuating washer and a smaller part near the proximal end of the actuating washer;
        a resisting resilient element clamped between an inside wall of the body of the barrel and the proximal end of the actuating washer; and
        an actuating resilient element mounted in the sleeve and pressed against the cap;
    a high-pressure air source mounted slidably in the body of the barrel, selectively blocked by the actuating unit, selectively actuated by the actuating unit to slide toward the second end of the barrel to hit the piercing needle, and having a body and a neck, wherein an outer diameter of the neck is smaller than an outer diameter of the body, the outer diameter of the neck is larger than the inner diameter of the smaller part and is smaller than the inner diameter of the larger part of the through hole of the actuating washer.

2. The automatic injection device for fluid as claimed in claim 1, wherein the actuating resilient element abuts against the high pressure air source.

3. The automatic injection device for fluid as claimed in claim 1 further comprising a driven unit mounted slidably in the barrel, attached to the high-pressure air source and selectively actuated by the actuating unit to slide toward the second end of the barrel.

4. The automatic injection device for fluid as claimed in claim 3, wherein
    the driven unit has a piston attached to the high-pressure air source; and
    the actuating resilient element is claimed between the piston and the cap.

5. The automatic injection device for fluid as claimed in claim 4, wherein
    the driven unit comprises a washer secured on the piston; and
    the actuating resilient element is clamped between the washer and the cap.

6. The automatic injection device for fluid as claimed in claim 1, wherein
    the actuating washer has a mounting tag formed on the proximal end of the actuating washer; and
    the resisting resilient element is mounted around the mounting tag.

7. The automatic injection device for fluid as claimed in claim 2, wherein
    the actuating washer has a mounting tag formed on the proximal end of the actuating washer; and
    the resisting resilient element is mounted around the mounting tag.

8. The automatic injection device for fluid as claimed in claim 3, wherein
    the actuating washer has a mounting tag formed on the proximal end of the actuating washer; and
    the resisting resilient element is mounted around the mounting tag.

9. The automatic injection device for fluid as claimed in claim 4, wherein
    the actuating washer has a mounting tag formed on the proximal end of the actuating washer; and
    the resisting resilient element is mounted around the mounting tag.

10. The automatic injection device for fluid as claimed in claim 5, wherein
    the actuating washer has a mounting tag formed on the proximal end of the actuating washer; and
    the resisting resilient element is mounted around the mounting tag.

11. The automatic injection device for fluid as claimed in claim 1, wherein
    the body of the barrel has a slot formed through the second end of the body; and
    the piercing needle has a central hole communicating with the slot of the body.

12. The automatic injection device for fluid as claimed in claim 2, wherein
    the body of the barrel has a slot formed through the second end of the body; and
    the piercing needle has a central hole communicating with the slot of the body.

13. The automatic injection device for fluid as claimed in claim 3, wherein
    the body of the barrel has a slot formed through the second end of the body; and
    the piercing needle has a central hole communicating with the slot of the body.

14. The automatic injection device for fluid as claimed in claim 4, wherein
    the body of the barrel has a slot formed through the second end of the body; and the piercing needle has a central hole communicating with the slot of the body.

15. The automatic injection device for fluid as claimed in claim 10, wherein the body of the barrel has a slot formed through the second end of the body; and the piercing needle has a central hole communicating with the slot of the body.

16. The automatic injection device for fluid as claimed in claim 1, wherein the resilient element is a spring.

17. The automatic injection device for fluid as claimed in claim 2, wherein the resilient element is a spring.

18. The automatic injection device for fluid as claimed in claim 3, wherein the resilient element is a spring.

19. The automatic injection device for fluid as claimed in claim 15, wherein the resilient element is a spring.

\* \* \* \* \*